(12) United States Patent
Ring

(10) Patent No.: US 9,918,838 B2
(45) Date of Patent: Mar. 20, 2018

(54) INTEGRATED CATHETER GUIDE WIRE CONTROL DEVICE

(71) Applicant: Michael Ring, Spokane, WA (US)

(72) Inventor: Michael Ring, Spokane, WA (US)

( * ) Notice: Subject to any disclaimer, the term of this patent is extended or adjusted under 35 U.S.C. 154(b) by 0 days.

(21) Appl. No.: 15/473,608

(22) Filed: Mar. 30, 2017

(65) Prior Publication Data

US 2017/0209267 A1    Jul. 27, 2017

Related U.S. Application Data

(63) Continuation-in-part of application No. 15/005,520, filed on Jan. 25, 2016.

(60) Provisional application No. 62/315,669, filed on Mar. 31, 2016.

(51) Int. Cl.
     *A61M 25/00*      (2006.01)
     *A61F 2/24*      (2006.01)
     *A61M 25/09*      (2006.01)

(52) U.S. Cl.
     CPC .......... *A61F 2/2436* (2013.01); *A61F 2/2418* (2013.01); *A61M 25/09041* (2013.01); *A61M 2025/09125* (2013.01)

(58) Field of Classification Search
     CPC .... A61M 2025/09125; A61M 25/0113; A61M 25/09041; A61F 2/2427; A61F 2/2418; A61F 2/2436

USPC ......................................................... 604/528
See application file for complete search history.

(56) References Cited

U.S. PATENT DOCUMENTS

| | | | |
|---|---|---|---|
| 5,304,131 A * | 4/1994 | Paskar .............. | A61M 25/0041 600/435 |
| 6,752,800 B1 * | 6/2004 | Winston .......... | A61M 25/09041 604/157 |
| 7,892,186 B2 * | 2/2011 | Soukup ............. | A61M 25/0136 600/585 |
| 8,388,521 B2 * | 3/2013 | Byers ..................... | A61B 1/018 600/154 |
| 8,992,480 B2 | 3/2015 | Gallacher et al. | |

OTHER PUBLICATIONS

MEDTRONIC, www.corevalve.com/us/index.htm web page for CoreValve device, downloaded and printed to .pdf on Mar. 23, 2017.

* cited by examiner

*Primary Examiner* — Jason Flick
(74) *Attorney, Agent, or Firm* — KnuBox, LLC

(57) ABSTRACT

A guide wire control device and methods of use are described herein. A guide wire is retained by a lock mechanism to a translating assembly within a stationary tubular structure. A rotating actuator controls the translation of the translating assembly and resulting guide wire. The guide wire control device provides improved control of guide wires and angles of a deployment capsule during transcatheter surgical procedures.

20 Claims, 16 Drawing Sheets

INTEGRATED CATHETER GUIDE WIRE CONTROL DEVICE

CROSS REFERENCE TO RELATED APPLICATION

This application claims the benefit of pending U.S. provisional application Ser. No. 62/315,669 filed Mar. 31, 2016 by the present inventor, which is incorporated by reference in its entirety.

This application is also a continuation-in-part of pending U.S. application Ser. No. 15/005,520 filed Jan. 25, 2016 by the present inventor, which is incorporated by reference in its entirety.

STATEMENT REGARDING FEDERALLY SPONSORED R&D

Not related to this application.

TECHNICAL FIELD

This invention relates to guide wire control devices, and more particularly to guide wire control devices for use in procedures involving catheter deployed medical devices.

BACKGROUND OF THE INVENTION

Guide wires are commonly used in the field of medicine. They are used to navigate the torturous pathways of anatomy. Guide wires, also called stylets, can be inserted through an orifice of a body, or surgically inserted. The wire is pushed, turned, and flexed at a proximal end which remains outside the body. The forces applied to the proximal end translate down the wire to a distal end. The distal end can provide various procedure specific functions inside the body. A guide wire can be made from various materials, with metal being most common. Guide wires also come in a wide range of diameters, typically being 0.050 inches or less. Guide wire coatings and finishes can provide additional benefits for a given procedure. A common application for a guide wire is with endovascular procedures.

The practice of repairing an artery through the use of a stent is well known in the field of medicine. In general and as an example of a typical guide wire application, a guide wire is inserted into an artery using the Seldinger technique. The femoral artery, near the groin, is a common entry point. The guide wire is advanced to a desired location. A delivery catheter with a stent attached is placed around the guide wire through a central lumen and is advanced along the length of the guide wire. Depending on the type of stent, the stent may be deployed by expansion of a balloon or in the case of nitinol stents, by withdrawing a sheath covering the nitinol stent and allowing the nitinol stent to assume its memory shape through self-expansion. A well-known issue with self-expanding nitinol stents is their tendency to "jump" as the sheath on the delivery catheter is retracted, which limits the precision of the stent deployment and can result in malposition of the stent. Once the stent is deployed, the delivery catheter is removed from the body.

A recent advancement in the treatment of cardiac disease is transcatheter devices to either replace or repair dysfunctional native or prosthetic cardiac valves. These include the aortic, mitral, tricuspid and pulmonary valves. Rather than using an open heart procedure to replace or repair a defective valve in a patient's heart, a minimally invasive catheter system is used to deliver and deploy an expanding structure (typically a stent-like device) containing a replacement valve. The new prosthetic valve displaces the leaflets of the defective valve and takes over the function of regulating blood flow through the heart and artery. Transcatheter prosthetic valve technology is dominated by two technologies. The first uses a stainless steel (or other similar metal composition) stent that is expanded by an inflatable balloon. The second utilizes a nitinol metallic mesh that is cooled and compacted, and then expands to a desired shape and size when the metal approaches body temperature.

Transcatheter valve replacement presents marked challenges over other endovascular procedures that utilize a catheter. Unlike typical endovascular procedures which occur in constrained tubular blood vessels where there is limited spatial movement of the devices, transcatheter valve procedures by their nature are performed in the heart with relatively large and spatially complicated chambers that pose significant challenges to guidewire management and device manipulation by the surgeon. First, the prosthetic valve must be located extremely precisely relative to the natural valve prior to the prosthetic valve being expanded in place. The replacement valve needs to be located plus or minus 1-3 mm in depth relative to its target location at the valve annulus. The surgeon may use fluoroscopic and ultrasound imaging to determine optimal depth of the valve prior to deployment. From the proximal end, the surgeon manipulates the guide wire and catheter sheath to achieve the desired deployment location of the prosthetic valve. An improperly deployed valve can lead to perivalvular regurgitation or catastrophic embolization of the device into either the heart or aorta. Secondly, in order to minimize canting of the prosthetic valve, the deployed valve should be positioned ideally in the center and coaxially within the diseased native valve. Again, the surgeon uses forces on the proximal end of the guide wire and catheter to attempt to manipulate the location of the valve relative to the walls of the defective valve. Third, during the procedure the surgeon in addition to maintaining optimal forces on both the catheter sheath and guide wire, has additional responsibilities of managing the operating room, and monitoring fluoroscopic, hemodynamic and other monitors. When the replacement valve is optimally located, the surgeon must maintain optimal pressure on both the guide wire and the catheter to resist translational forces created by the expanding valve. Wherein many endovascular procedures utilize the guide wire only for navigation purposes, in new advanced procedures such as transcatheter aortic valve replacement, the guide wire is often the key element throughout the procedure and requires constant attention. The transcatheter aortic valve replacement guide wire provides navigation of the catheter sheath as well as impacting location of the deployed valve. With guide wires being small in diameter, often coated in low friction materials, and with bodily fluids present, maintaining optimal pressure on the guide wire throughout the valve replacement procedure can be challenging and fatiguing for the surgeon. Although the field of transcatheter mitral and tricuspid valve replacement and repair is less mature than transcatheter aortic valve replacement, the challenges of accurate device deployment may be even greater due to the factors outlined above.

In these respects, the present invention departs from conventional concepts of the prior art by providing a guide wire control device for use in catheter based medical procedures. The present invention also provides an improved way to achieve optimal valve deployment in transcatheter valve replacement and repair procedures.

SUMMARY OF THE INVENTION

The present invention takes a very different approach to controlling a guide wire during medical procedures in comparison to the prior art.

The present invention provides a device for controlling a guide wire during a surgical procedure. The proximal end of a guide wire is retained by a releasable lock mechanism to a translational assembly. The translational assembly moves relative to a stationary assembly. The movement of the translational assembly, and resulting guide wire, is controlled by a rotating actuator that gives the user precise control of the resulting movement of the guide wire.

Control of a guide wire, according to the present invention, provides the advantages of reducing fatigue of the surgeon and better locational accuracy of catheter delivered medical devices. The preferred embodiments for both the apparatus and process is described for use in heart valve repair and replacements, but the present invention is applicable to any medical procedure utilizing a catheter.

Also described in the present invention are nonlinear shapes in the proximity of the distal end of the guide wire, which depending on wire stiffness and shape can facilitate a change in orientation of the delivery capsule relative to the cardiac or other anatomy. The resulting trajectory and position changes of the delivery capsule provides the ability to more accurately place a prosthetic heart value in optimal locations within the heart.

Although described for use in heart valve replacement and repairs as part of the best mode of the present invention, optimizing guide wires as described herein is applicable to any guide wire based medical procedure.

These and other features, aspects, and advantages of the present invention will become better understood with regard to the following description, appended claims, and accompanying drawings.

BRIEF DESCRIPTION OF THE DRAWINGS

Preferred embodiments of the invention are described below with the reference to the following accompanying drawings.

DETAILED DESCRIPTION OF THE PREFERRED EMBODIMENTS

Many of the fastening, connection, wiring, control, manufacturing and other means and components utilized in this invention are widely known and used in the field of the invention, and their exact nature or type is not necessary for a person of ordinary skill in the art or science to understand the invention; therefore they will not be discussed in detail. Furthermore, the various components shown or described herein for any specific application of this invention can be varied or altered and anticipated by this invention and the practice of a specific application or embodiment of any element may already be widely known or used in the art, or persons skilled in the art or science; therefore, each will not be discussed in significant detail.

The present invention, as described, is used to control guide wires during medical procedures. Guide wires can be used to navigate tortuous pathways, can be used in advance of a delivery catheter, or used in conjunction with a delivery catheter to perform a desired medical procedure. Although the present invention is primarily described for use within an aortic artery, it should be appreciated that the present invention should not be construed to be limited to any particular body lumen. Other applicable lumens include, but are not limited to, gastrointestinal and urine lumens. Similarly, the present invention is primarily described for use with heart valve replacement procedures, but the present invention should not be construed to be limited to any particular procedure. Other applicable procedures include, but are not limited to, coronary angioplasty, stenting procedures and angiograms.

Figure 1:
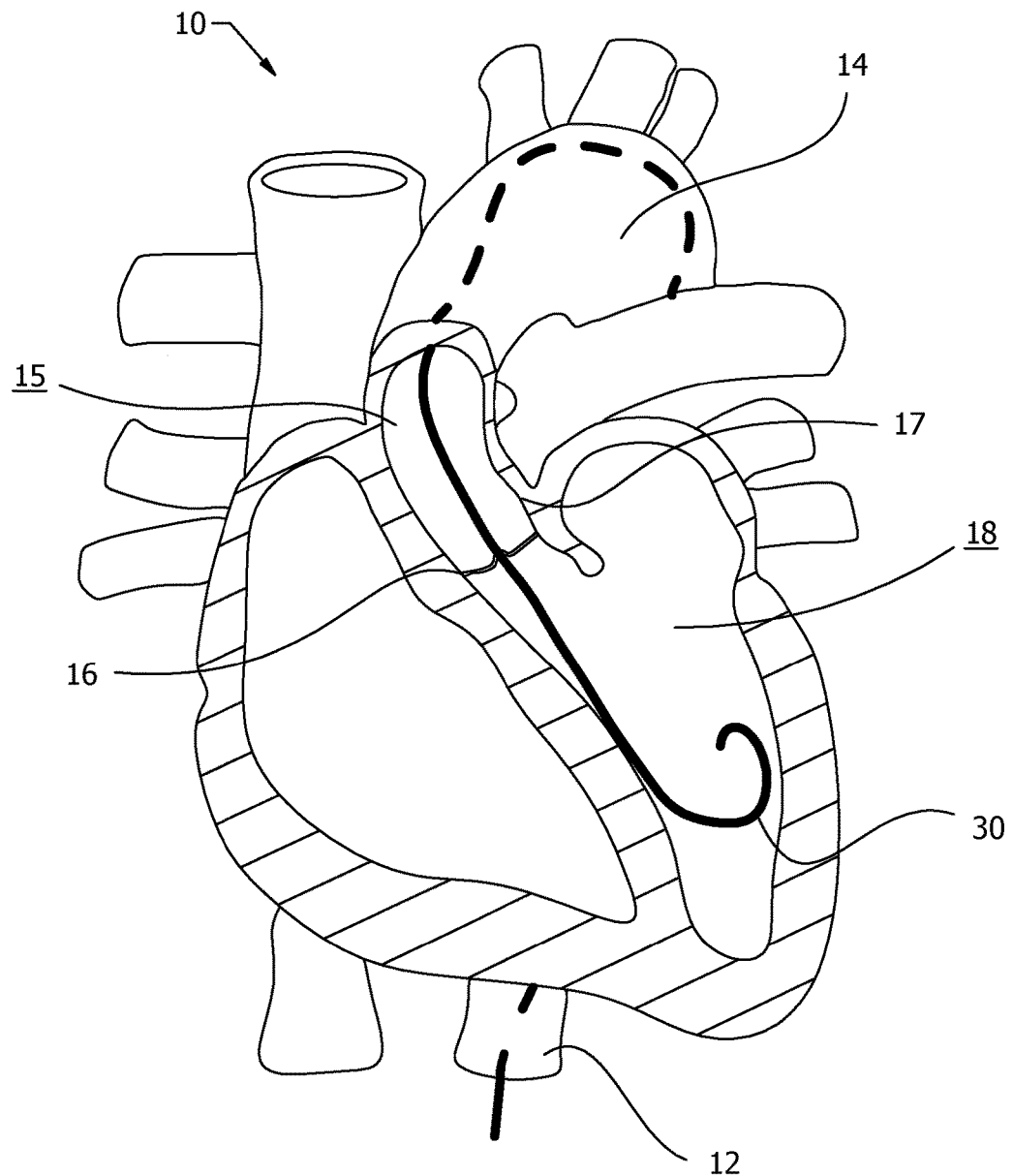
FIG. 1 is a front partial section view of a heart with a guide wire inserted through the aortic artery and into the left ventricle of the heart.
Figure 2:
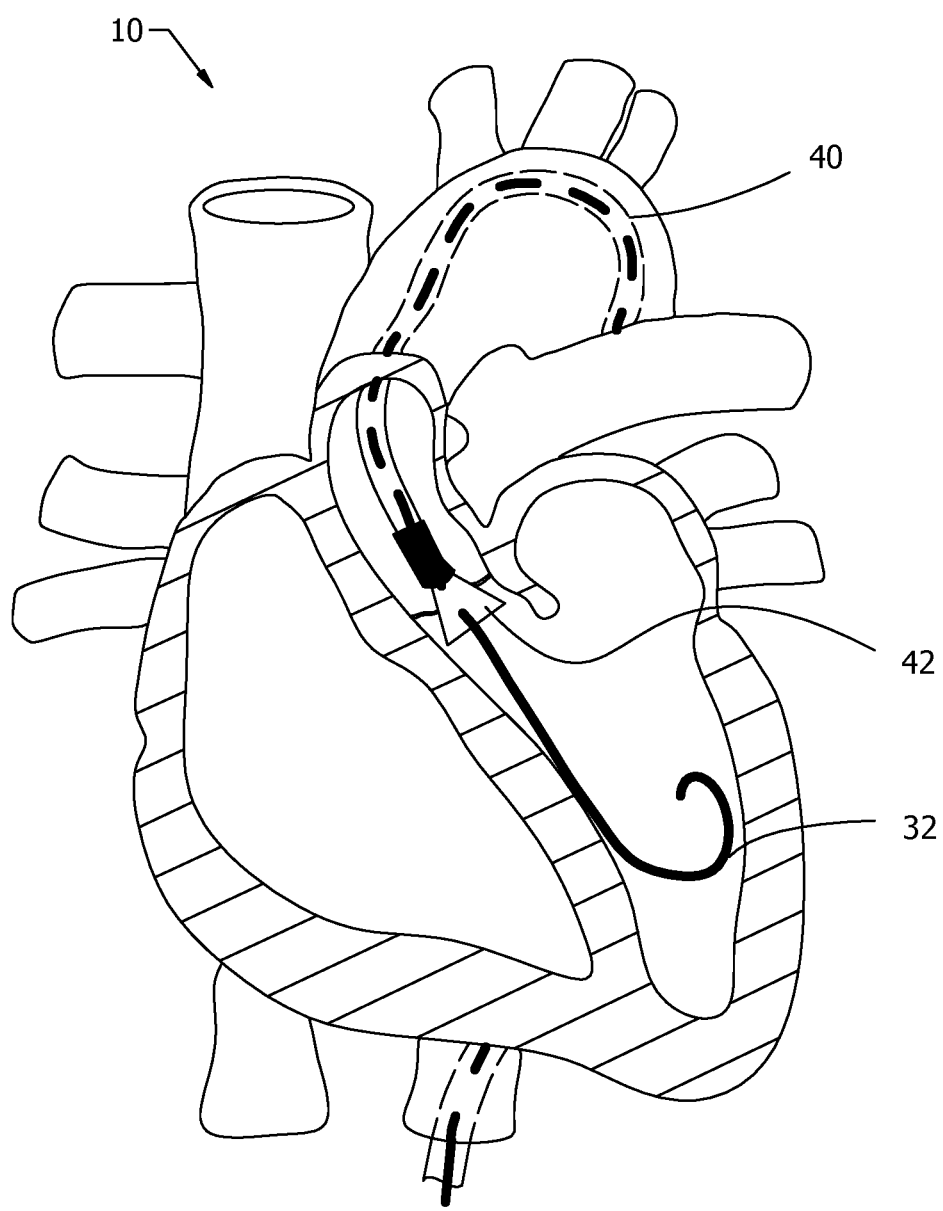
FIG. 2 is the same front partial view as FIG. 1, but with a catheter sheath and artificial valve inserted around the guide wire of FIG. 1 and into the heart.
Figure 3:
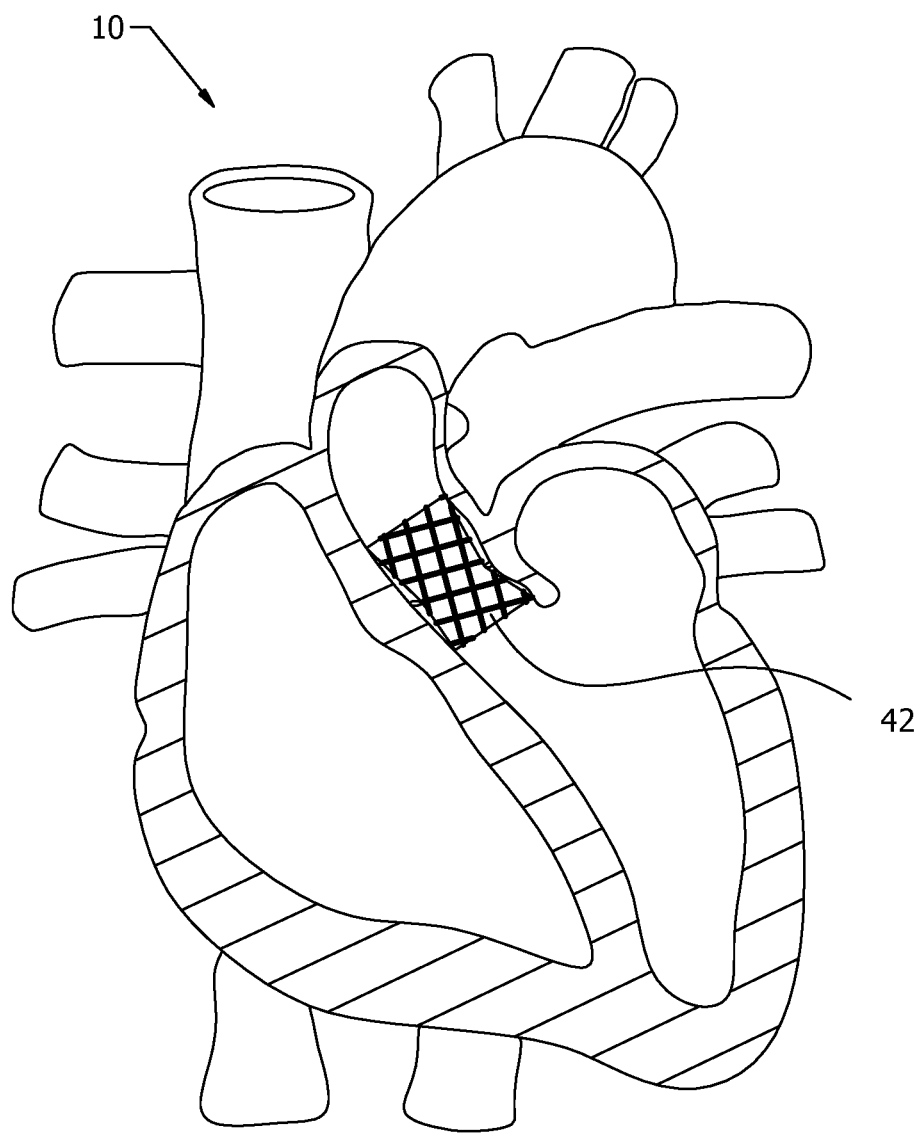
FIG. 3 is the same front partial section view of FIG. 1 and showing a deployed artificial valve.

Now referring to the figures, FIGS. 1, 2 and 3 show a partial section view of a heart 10. The anatomy of heart 10 is well known in the art of medicine and a detailed understanding is not necessary for one to understand and appreciate the present invention; therefore it will not be described in significant detail. Components of heart 10 shown in the accompanying drawings are in the non-limiting context of using the present invention in an aortic valve replacement procedure.

In replacing an aortic valve and referring to FIG. 1, a guide wire 30 is advanced through an aortic artery 12, through a natural aortic valve 16, and into a left ventricle 18. Aortic artery 12 starts in the abdomen. An aortic arch section 14 comes from the back side of the heart and bends towards an ascending aorta section 15 which is just before aortic valve 16. Blood leaving left ventricle 18 escapes through natural aortic valve 16. Aortic valve 16 is surrounded by an aortic valve annulus section 17. It should be appreciated that the lumens of heart 10 are complex in shape and trajectory.

Figure 4:
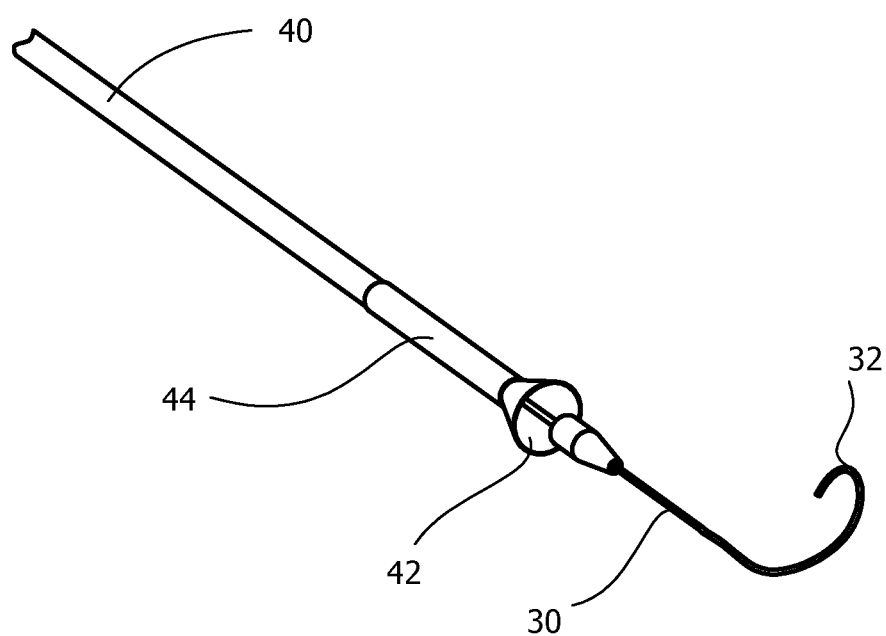
FIG. 4 is a perspective view showing a distal end of a prior art sheath, capsule and valve.

FIG. 4 shows the distal end of a prior art heart valve replacement delivery system. Although the present invention is not limited to any particular delivery system, one such system is commercially produced by MEDTRONIC® under the tradename COREVALVE®. Guide wire 30 has a guide wire distal end 32 which is shown manufactured with a flexible curl. Guide wire 30 is approximately 0.035 inches in diameter and made from a metallic material which is coated in a low friction material, such as polytetrafluoroethylene. Guide wire distal end 32 is more flexible than the rest of guide wire 30 which allows it to more easily navigate tortuous pathways with minimal damage to adjacent tissue. A catheter sheath 40 is advanced over guide wire 30. Catheter sheath 40 is connected to a capsule 44 which houses a prosthetic valve 42. In FIG. 4, prosthetic valve 42 is shown in a partially deployed state. With advancement of catheter sheath 40, prosthetic valve 42 is completely encapsulated within capsule 44. With retraction of catheter sheath 40, prosthetic valve 42 is deployed.

The application of the prior art heart valve delivery system of FIG. 4 is shown in FIGS. 1, 2 and 3. In FIG. 1, guide wire 30 has been advanced through aorta 12, has navigated both aortic arch 14 and ascending aorta 15 sections, has penetrated though natural valve 16, and has guide wire distal end 32 located within left ventricle 18. The curve of distal end 32 is shown against a wall of left ventricle 18 which can provide some force against guide wire 30. It should be appreciated at the stage of FIG. 1, the surgeon has advanced guide wire 30 by applying forces to the proximal end of guide wire 30. Imaging and feel ensures guide wire 30 is properly placed in heart 10. Guide wire 30, when placed in heart 10, has some impact to the normal function of heart 10. Therefore, it is desirable for the surgeon to act quickly and precisely to deploy prosthetic valve 42.

FIG. 2 shows catheter sheath 40 advanced over and along guide wire 30. Because guide wire 30 is used in conjunction with catheter sheath 40 to locate prosthetic valve 42 in its optimal location, it should be appreciated that the surgeon may have to move guide wire 30 in relationship to catheter sheath 40. Optimal location of prosthetic valve 42 in relationship to natural valve 16 and aortic annulus section 17 may be plus or minus one to three millimeters. Once optimal location of prosthetic valve 42 has been achieved both radially and in depth, the surgeon retracts catheter sheath 40 causing deployment of prosthetic valve 42. The angled expansion of prosthetic valve 42 can cause a "jump" translation of either catheter sheath 40, guide wire 30, or both, during deployment. Translations during deployment can negatively impact deployment of prosthetic valve 42. To maintain a successful deployment of prosthetic valve 42, the surgeon must maintain optimal locations and forces of both catheter sheath 40 and guide wire 30. FIG. 3 shows prosthetic valve 42 deployed.

Figure 5:
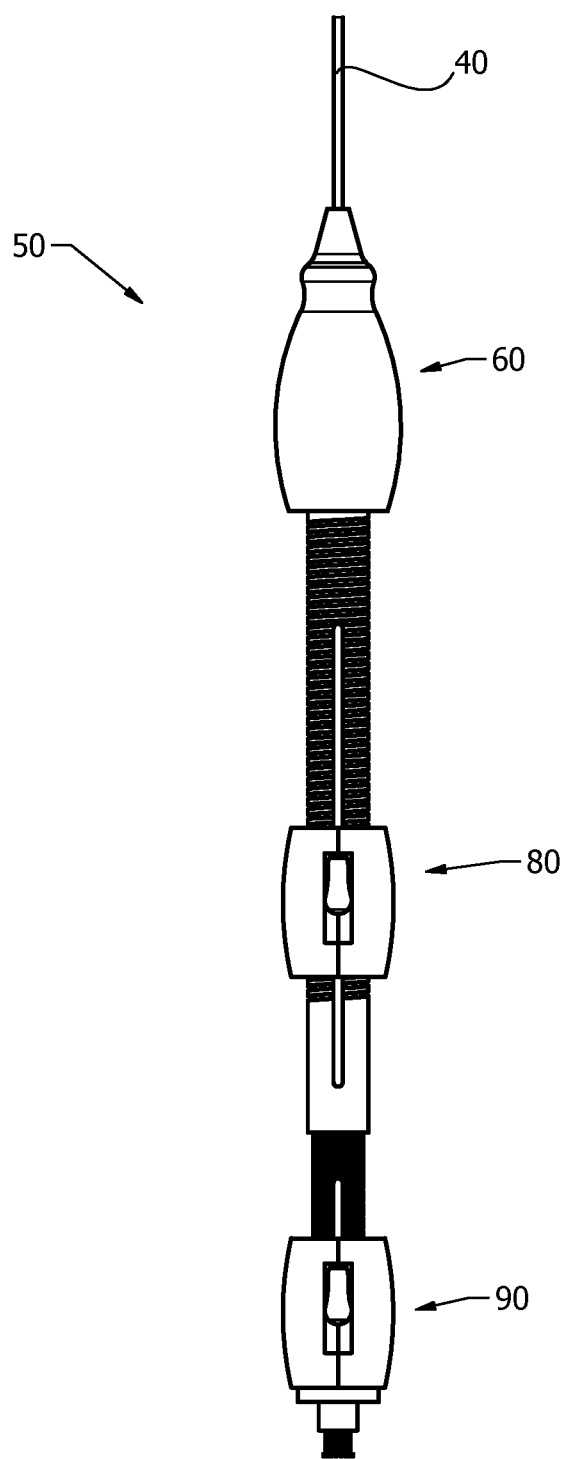
FIG. 5 is a top view of a proximal end of a novel heart valve deployment device according to the present invention.
Figure 6:
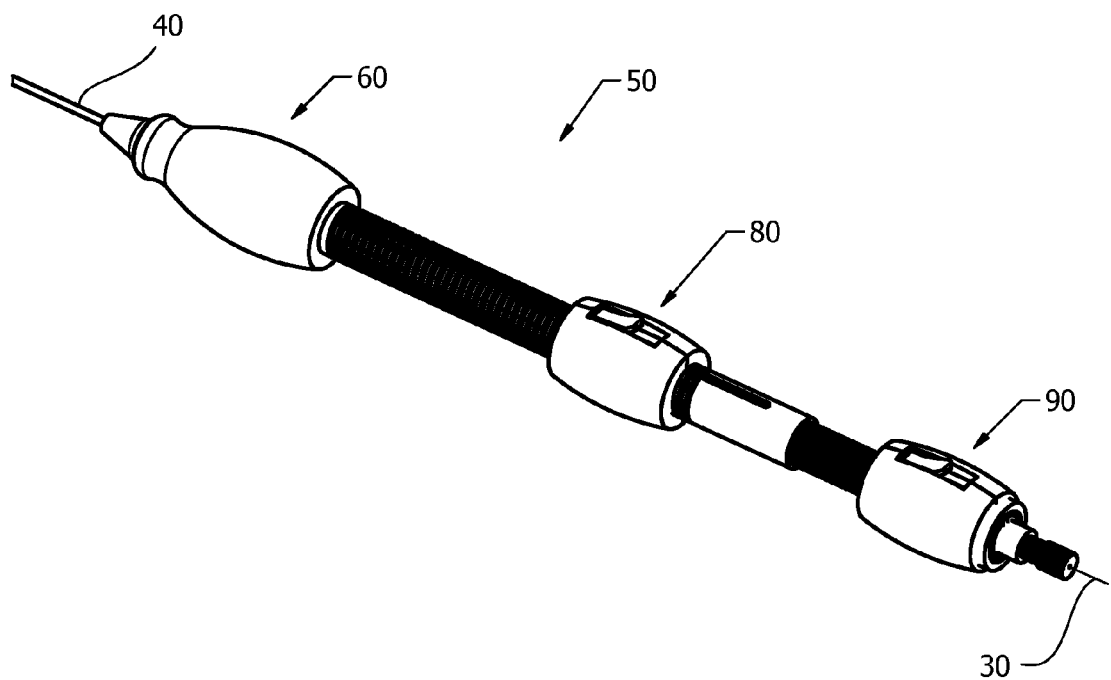
FIG. 6 is a perspective view of the deployment device of FIG. 5.

FIGS. 5 and 6 show the overall present invention of a novel heart valve deployment device 50. Deployment device 50 is comprised of a stationary handle 60, a sheath manager 80 and a wire manager 90. Similar to the prior art MEDTRONIC® COREVALVE® deployment device, sheath 40 is connected to sheath manager 80. Sheath manager 80 rotates around stationary handle 60 causing both sheath manager 80 and a hollow tube 45 within sheath 40 to translate. A sheath slot 66 engages with sheath manager 80 so that only linear translation of sheath 40 occurs. Sheath manager 80 provides the means to control the translation of prosthetic valve 42 within capsule 44. Novel guide wire manger 90 provides the means to control the translation of guide wire 30 and to facilitate optimal location of valve 42 in the heart.

Figure 7:
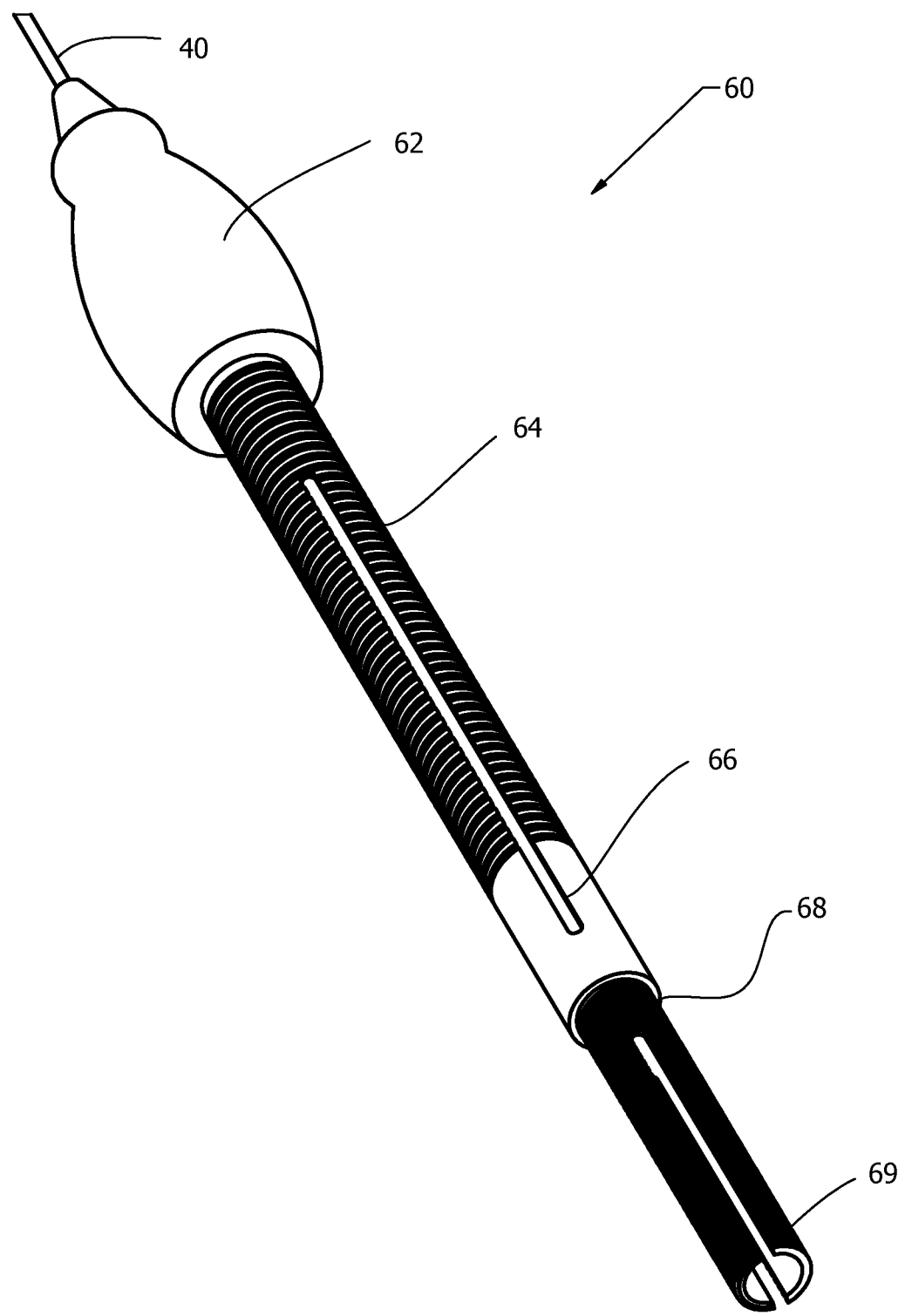
FIG. 7 is a perspective view of the deployment device main body having two threaded sections.

FIG. 7 shows stationary handle 60 which is preferably molded from plastic. A grip body 62 is used to provide stability to the overall system. During use, a surgeon's hand is in contact with grip body 62 to resist rotation and translation of stationary handle 60. Connected to grip body 62 is a sheath threads 64. Running through opposite sides of sheath threads 64 is sheath slot 66. Towards the back end of stationary handle 60 is a wire thread 68 and wire slot 69. To give approximate sizing but not intended to be limiting, grip body 62 is roughly 5 inches in length and has a major diameter of 1.75 inches. Threads 64 and 68 are approximately 0.050 inches wide, 0.040 inches deep and having approximately 10 threads per inch.

Figure 8:
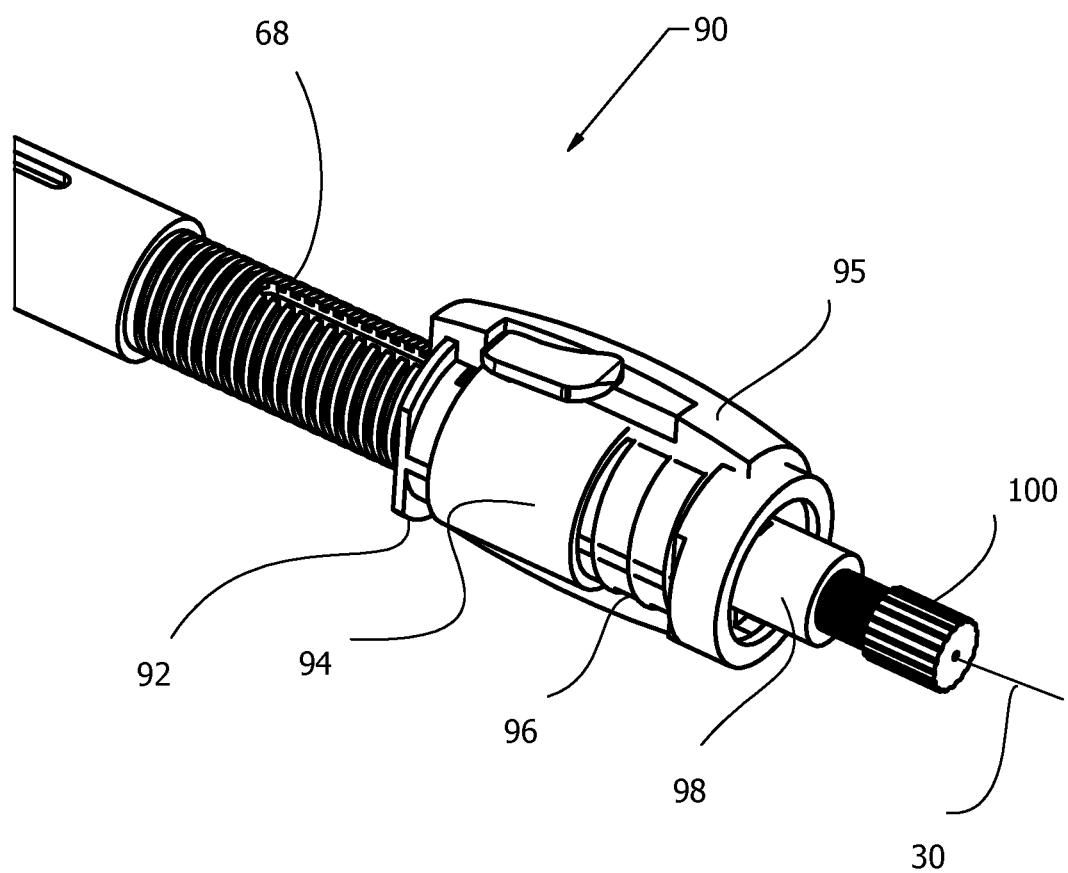
FIG. 8 is a perspective view of the guide wire control device and having a partial section view of the wire manager showing how the sleeve engages with the cover and actuator.

FIG. 8 shows the details of novel guide wire manager 90. Guide wire manager 90 is comprised of a cover 95, a cap 100, a carrier 98, a spring 96, an actuator 94, and a sleeve 92. Guide wire manager 90, and the rotation of cover 95 with respect to stationary handle 60 drives linear translation of guide wire 30. Shown in FIGS. 9 and 10, sleeve 92 has two instances of a tab 92a. Tab 92a engages with wire threads 68. Tab 92a is naturally biased to not engage with wire threads 68. With spring 96 applying a force to actuator 94 and moving it forward over tab 92a, tab 92a is deflected downward to engage with threads 68. A user applying a rearward force to a grip 94a causes actuator 94 to compress spring 96, translate rearward, and to allow tab 92a to return to its natural non-engaged position relative to wire threads 68. With tab 92a in its natural non-engaged position, guide wire manager 90 may spin freely or be removed from stationary handle 60. Spring 96 only needs to create enough force to deflect tab 92a in the engaged position within wire threads 68.

Sleeve 92 includes a flange 92b and a flat section 92d. Flange 92b engages with a groove 95a of cover 95 to keep sleeve 92 fixed to cover 95. A flat edge 95b of cover 95 engages with flat section 92d to force sleeve 92 to rotate with cover 95. It should be appreciated that with a user holding grip body 62 fixed, and rotating cover 95, that tab 92a rotates around threads 68 causing controlled linear translation of wire manger 90 and guide wire 30. It should further be appreciated that with a user applying a backward force to grip 94a, tab 92a is allowed to deflect out of threads 68 and guide wire manager 90 and guide wire 30 are free to slide or rotate relative to threads 68. With wire slot 69 extending through the back end of stationary handle 60, wire manager 90 and guide wire 30 are able to be quickly decoupled from stationary handle 60 during a procedure.

Figure 9:
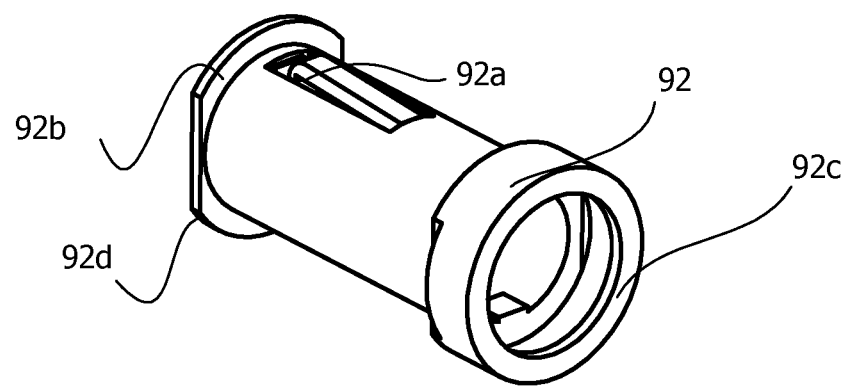
FIG. 9 is a rear perspective view of the sleeve of FIG. 8.
Figure 10:
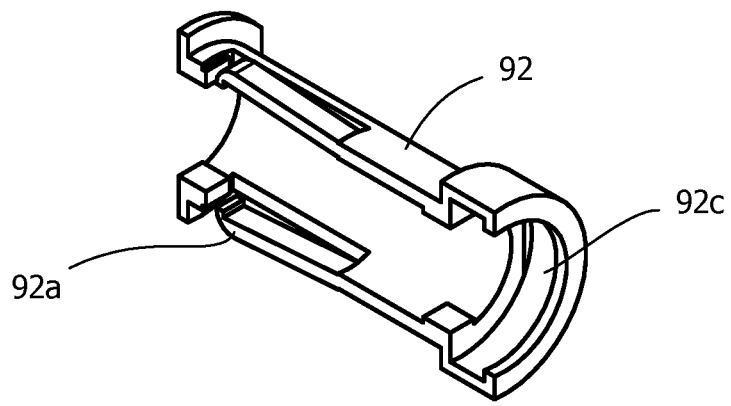
FIG. 10 shows one half of the sleeve of FIG. 9.
Figure 11:
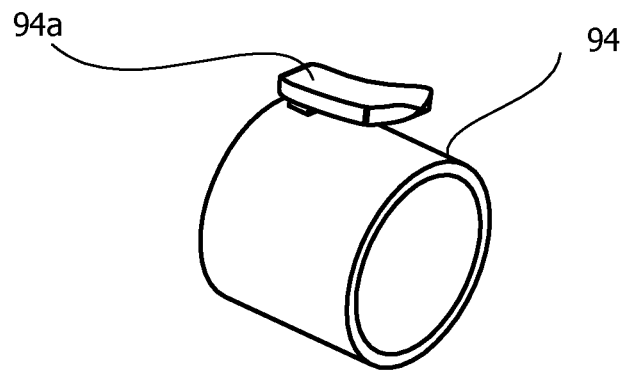
FIG. 11 is a rear perspective view of the actuator of FIG. 8.
Figure 12:
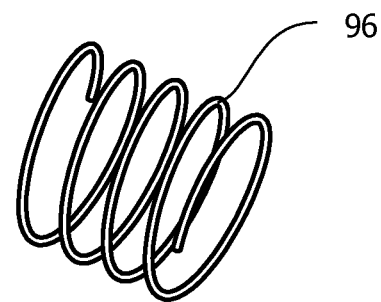
FIG. 12 is a rear perspective view of the spring of FIG. 8.
Figure 13:
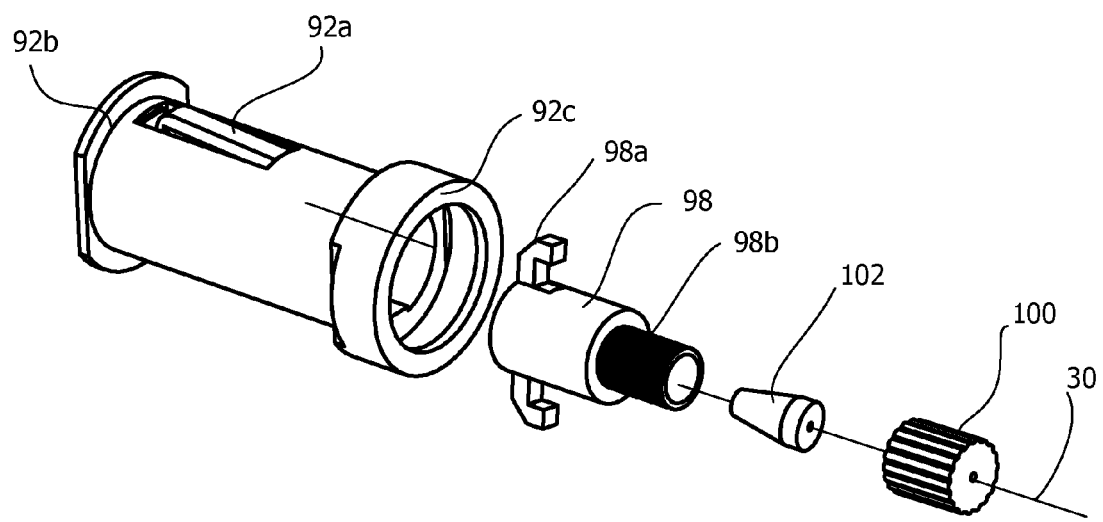
FIG. 13 is an exploded view of the wire carrier and how it fits into the sleeve.
Figure 14:
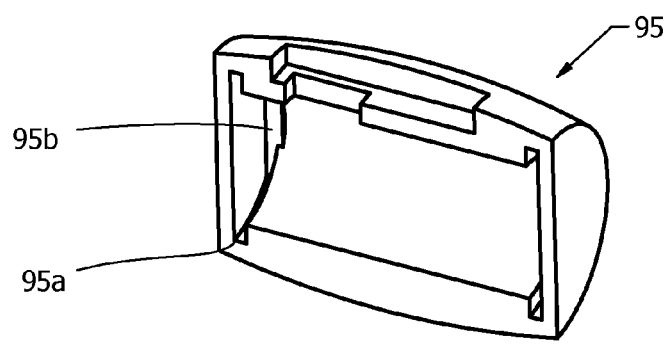
FIG. 14 shows one half of the cover and features for engaging with the sleeve of FIG. 9.
Figure 15:
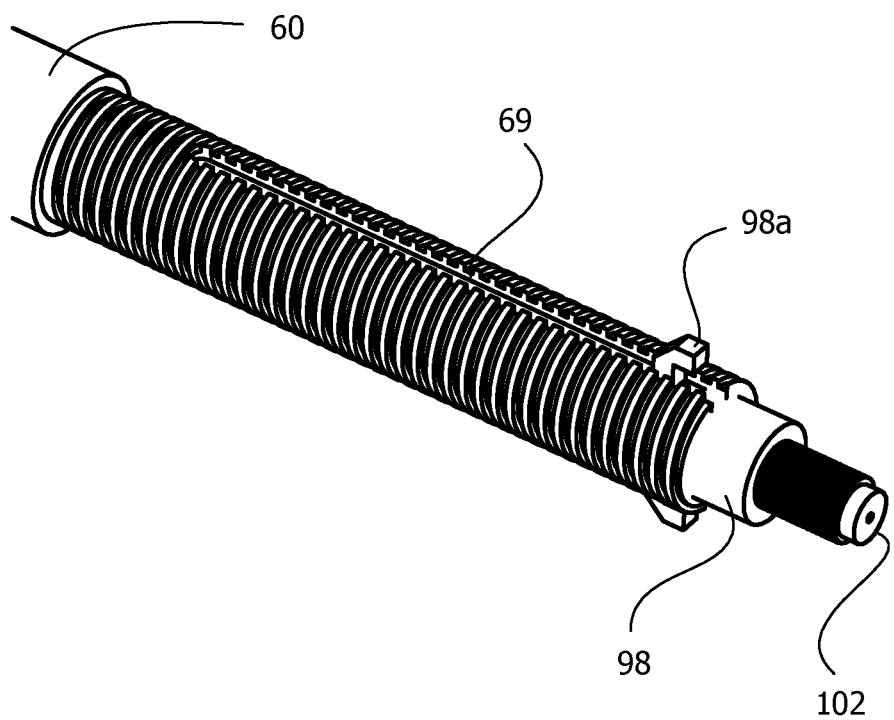
FIG. 15 is a partial perspective view of the threaded section of the stationary handle and showing the wire carrier, and tabs, sliding in the wire slot.

As shown in FIGS. 9 and 10, sleeve 92 includes a clip section 92c. As shown in FIG. 13, clip section 92c engages with a plurality of flanges 98a of carrier 98. Carrier 98 is inserted into clip section 92c with flanges 98a deflecting and then snapping outward into clip section 92c. Alternatively, clip section 92c can be an attached member to sleeve 92 or carrier 98 can be created by joining two halves. The result is that sleeve 92 is able to rotate freely around carrier 98 so that guide wire 30 only translates linearly. Linear motion is maintained because flanges 98a protrude through wire slot 69 of stationary handle 60. On the rear portion of carrier 98 is carrier threads 98b. Carrier threads 98b engage with cap 100 wherein rotation of cap 100 causes compression of a tube 102 around guide wire 30. The angle of tube 102 against the corresponding cavity within carrier 98 creates a friction force on guide wire 30. Preferably tube 102 is made from a rubber material and having a hole diameter of a couple of thousands of an inch larger than guide wire 30.

To use the device with respect to guide wire management, the surgeon can freely move guide wire 30 relative to deployment device 50 when cap 100 is not creating a compression on tube 102. With guide wire 30 in close proximity to the desired location within the patient, guide wire 30 is secured to deployment device 50 by turning cap 100 and creating a frictional force between guide wire 30 and tube 102. Rotating cover 95 turns sleeve 92 thus causing a screw force between tab 92a and wire threads 68. The screw force creates a linear translation to wire carrier 98. During the procedure and as needed, the surgeon can rotate cover 95 in either direction causing forward and backward translation of guide wire 30. At any time the surgeon can apply a rearward force to grip 94a and freely move wire manager 90, or decouple it from stationary handle 60.

In comparison to the prior art delivery devices wherein the doctor must use their fingers to try to control and secure guide wire 30, deployment device 50 of the present invention, and the co-invented guide wire controller of pending U.S. patent application Ser. No. 15/005,520 herein incorporated in its entirety by this reference, provide the means to securely and predictably translate guide wire 30. In addition to secured control, deployment device 50 and the referenced guide wire controller of the '520 application provide the means for a doctor, or user, to apply a greater translational force to guide wire 30 than they can accomplish with their fingers. Control and increased force creates opportunities to further improve alignment of capsule 44 within heart 10, and a more likely optimal location of valve 42 within heart 10.

Figure 16:
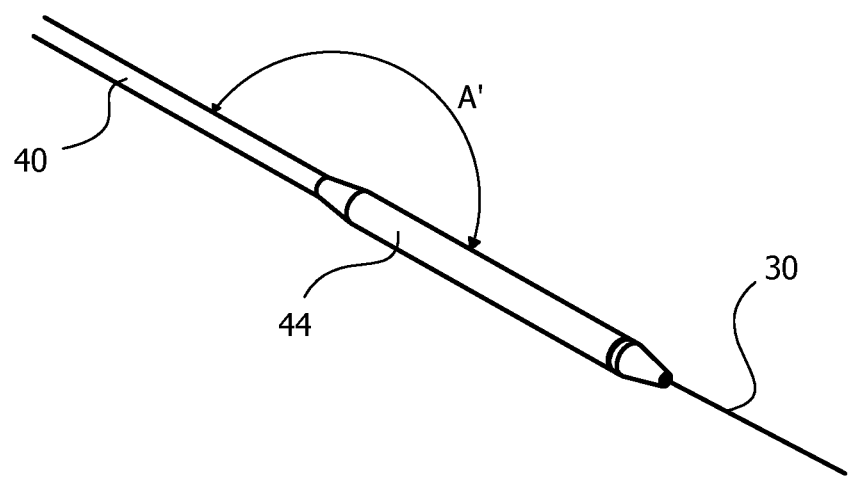
FIG. 16 is a partial perspective view of a prior art delivery capsule connected to the sheath in a linear relationship, and having a linear version of a guide wire.
Figure 17:
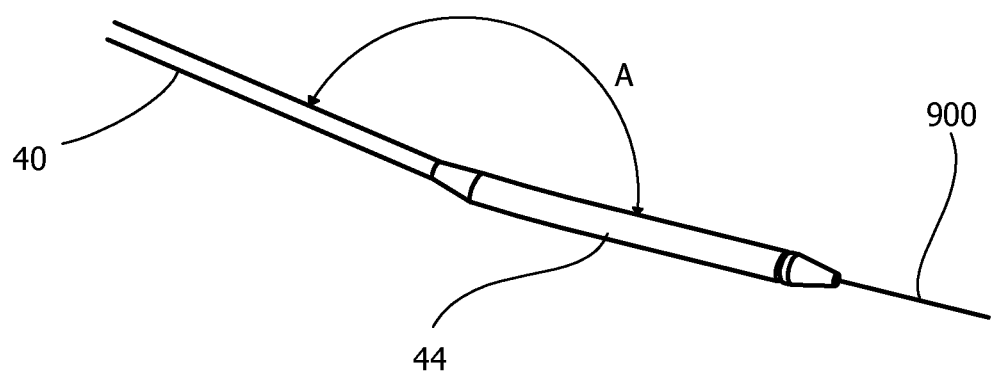
FIG. 17 is a partial perspective view of a delivery capsule connected to the sheath in a novel non-linear relationship caused by mechanical forces of a non-linear guide wire.

One such improvement is described in FIGS. 16 and 17. FIG. 16 shows a prior art delivery capsule 44 which is linearly aligned with the axis of sleeve 40 creating an angle A' which is equal to 180 degrees. With guide wire 30 being linear, translation of guide wire 30 does not cause any mechanical forces within. With prior art delivery devices, and wherein the doctor must try to control the guide wire manually by hand, it is desirable to minimize translation forces by reducing any friction between guide wire 30 and sheath 40. FIG. 17 shows a novel angled orientation of delivery capsule 44 with respect to sheath 40 caused by mechanical forces of a helical guide wire 900. An angle "A" exists between sheath 40 and capsule 44. Angle "A" is caused by a non-linear shape pre-formed into guide wire 900 prior to inserting it through delivery sheath 40. Because guide wires 30 and 900 are typically made from a rigid material, it has been found that the non-linear shape of helical guide wire 900 can create enough force to make angle "A" not equal to 180 degrees. It has also been found that small changes in translation of helical guide wire 900 can control the amount of change in angle "A". Deployment device 50 in combination with helical guide wire 900 allow capsule 44 to be angled as needed to be centered and with optimal trajectory to deploy valve 42 within heart 10.

Figure 24:
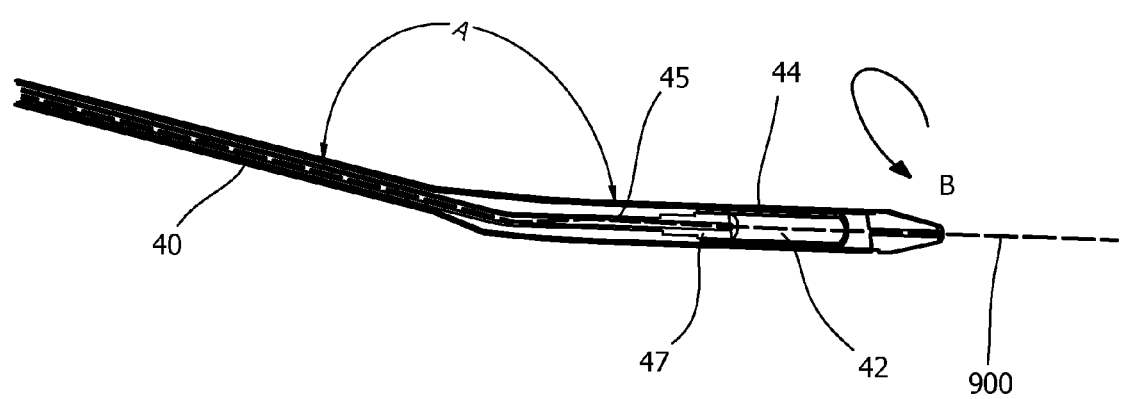
FIG. 24 is a partial perspective section view of the delivery capsule and sheath in a non-linear relationship with respect to each other.

FIG. 24 shows more detail on the interaction of guide wire 900 with capsule 44 and sheath 40. Within sheath 40 is hollow tube 45 that runs the length of sheath 40 and is attached to a valve connector 47 and to sheath manager 80. Valve connector 47 removably attaches to valve 42. Hollow tube 45 is connected to sheath manager 80 and pushes or pulls valve 42 within capsule 44 as needed for deployment of valve 42. Guide wire 30, or helical guide wire 900, is located within hollow tube 45. The nonlinear shape of helical guide wire 900 causes hollow tube 45 to want to bend with respect to sheath 40 creating a radial force between valve connector 47 and capsule 44, and a change in angle "A".

Figure 22:
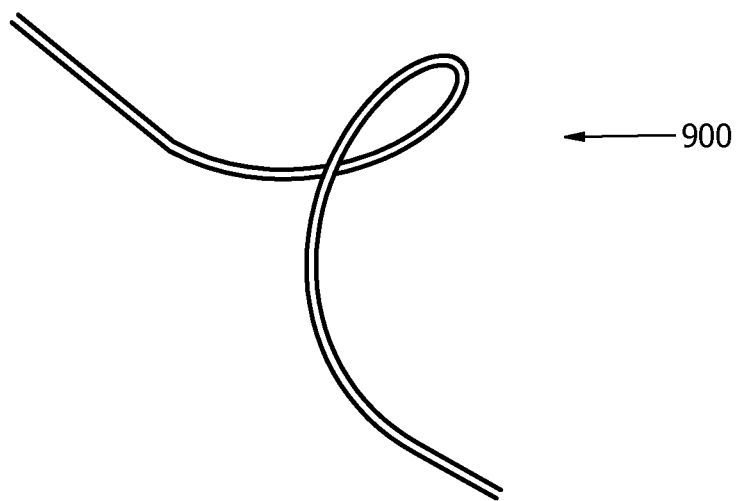
FIG. 22 side a partial perspective distal end view a helical guide wire alternative embodiment shape.
Figure 23:
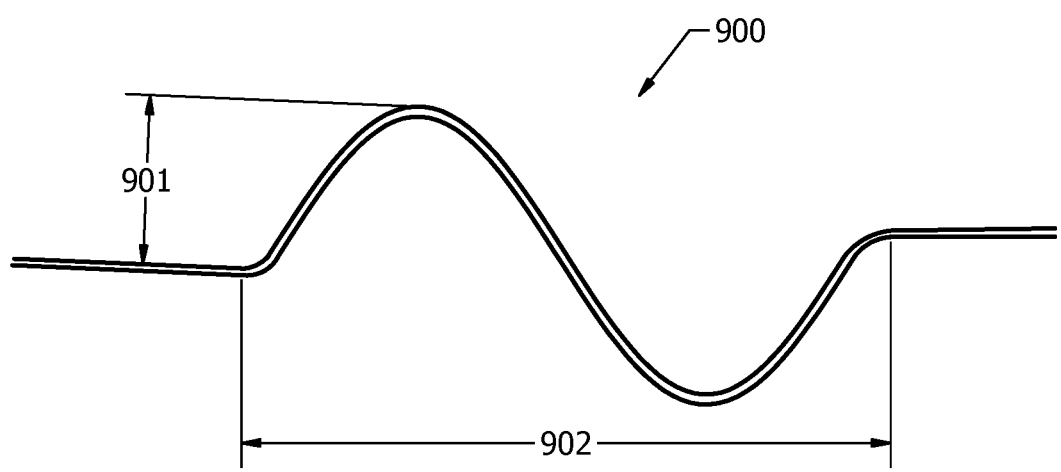
FIG. 23 side a partial side distal end view the helical guide wire alternative embodiment shape of FIG. 22.

Different wire shapes have been found to create different changes to the orientation of capsule 44 with respect to sheath 40. As shown in FIGS. 22 and 24, helical guide wire 900 has a coil radius 901 and a pitch 902. Although the present invention should not be construed to be limited to any particular dimension or range, it has been found that coil radius 901 being approximately one-half inch and coil pitch 902 being approximately one inch causes movement of capsule 44. Optimal dimensions for a given procedure or device are a function or desired translation force, guide wire material and guide wire diameter. As shown in FIG. 24, the helical shape of helical guide wire 900 creates both angle "A" being less than, or greater than, 180 degrees, but also creates a rotation "B" wherein angle "A" rotates around the axis of sheath 40. The translation of guide wire 900 through sheath 40 allows coil radius 901 to control angle "A" and causes coil pitch 902 to control rotation "B".

Although helical guide wire 900 has been found to be useful in providing a user control over the angle and rotation of capsule 44 with respect to sheath 40, the present invention should not be construed to be limited to such a shape.

Figure 18:
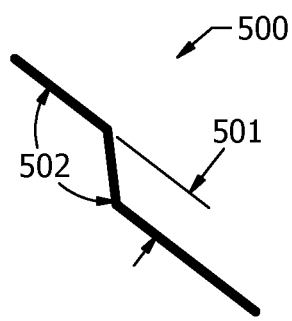
FIG. 18 is a partial side distal end view of an offset guide wire alternative embodiment shape.
Figure 19:
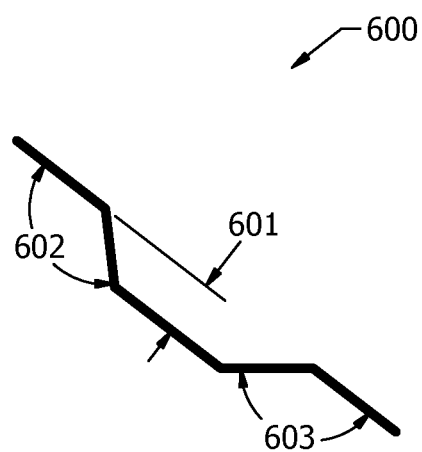
FIG. 19 is a partial side distal end view of a reversing offset guide wire alternative embodiment shape.
Figure 20:
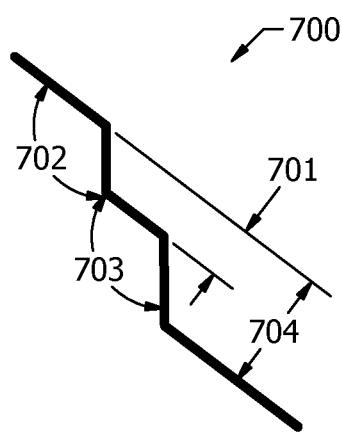
FIG. 20 is a partial side distal end view of a double offset guide wire alternative embodiment shape.
Figure 21:
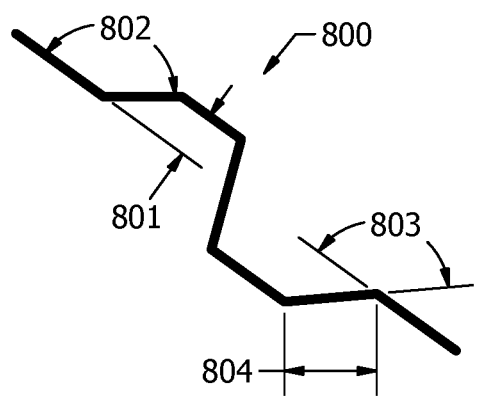
FIG. 21 is a partial side distal end view of a complex shaped guide wire alternative embodiment shape.

FIGS. 18 through 21 show more alternative embodiments of guide wire 30 with any one being optimal for a particular patient's heart or for a given procedure. FIG. 18 shows offset guide wire 500 having an offset 501 and an angle 502 relative to the main guide wire axis. Offset 501 may be chosen to be ideally suited for a particular patient's heart or procedure, and to create a particular angle "A". FIG. 19 shows a reversing offset guide wire 600 having an offset 601 and an angle 602 relative to the main guide wire axis and a second angle 603. Offset 601 may be chosen to be ideally suited for a particular patient's heart or procedure. FIG. 20 shows a double offset guide wire 700 having a first angle 702 and a first offset 701 which is connected to a second angle 703 and having a second offset 704. As a further example, FIG. 21 shows a complex guide wire 800 having a plurality of bends and offsets that may be made in any direction of three dimensional space. A first offset 801 and a first dimensional angle 802 creates movement of capsule 44 in a first direction and a second movement direction is created by a second and rotated angle 803 and a second rotated offset 804. It should be appreciated that translation of guide wire 800 can move capsule 44 in different three dimensional planes as needed to optimally place valve 42.

While the catheter guide wire control device and related methods described herein constitute preferred embodiments of the invention, it is to be understood that the invention is not limited to these precise form of assemblies, and that changes may be made therein without departing from the scope and spirit of the invention as defined in the appended claims.

The invention claimed is:

1. A guide wire control device comprising:
   a stationary member having a thread on an outside surface;
   a slot partially extending the length of said stationary member;
   a translating carrier at least partially within said stationary member and having at least one flange extending through said slot;
   a sleeve in rotational engagement with said thread and in linear engagement with said carrier; and,
   wherein said translating carrier includes a releasable lock mechanism for securing a guide wire.

2. The guide wire control device of claim 1, wherein said sleeve includes an actuator for disengaging said sleeve from said thread.

3. The guide wire control device of claim 1, wherein said releasable lock mechanism includes a threaded cap and a compression tube.

4. The guide wire control device of claim 1, wherein said guide wire includes an at least one offset.

5. The guide wire control device of claim 1, wherein said guide wire includes a helical section.

6. The guide wire control device of claim 1, wherein said sleeve is rotationally constrained to a cover.

7. A guide wire control device comprising:
   a stationary member having a thread on an outside surface;
   a slot partially extending the length of said stationary member;
   a translating carrier within said stationary member and having at least one flange extending through said slot;
   a sleeve having at least one flexible tab in rotational engagement with said thread, said sleeve also in linear attachment with said at least one flange; and,
   wherein said translating carrier includes a friction lock securing said carrier to a guide wire.

8. The guide wire control device of claim 7, wherein said sleeve includes an actuator for disengaging said at least one tab from said thread.

9. The guide wire control device of claim 7, wherein said friction lock includes a threaded member.

10. The guide wire control device of claim 7, wherein said guide wire includes an at least one angle.

11. The guide wire control device of claim 7, wherein said guide wire includes an at least one offset.

12. The guide wire control device of claim 7, wherein said guide wire includes an at least one helical section.

13. The guide wire control device of claim 7, wherein said sleeve is rotationally constrained to a cover.

14. A guide wire control device comprising:
   a stationary assembly in fixed relationship with a delivery catheter having a capsule, said stationary assembly having a sheath manager in linear connection with said capsule and a wire manager in linear connection with a guide wire extending through said capsule, said stationary member having a thread;
   a slot partially extending the length of said stationary member;
   a translating member within said stationary assembly and having at least one flange extending through said slot;
   a sleeve in rotational engagement with said threads and in linear engagement with said flange; and,
   wherein said translating member includes a releasable lock mechanism for securing said guide wire.

15. The guide wire control device of claim 14, wherein said guide wire includes a bend within said capsule.

16. The guide wire control device of claim 14, wherein said guide wire includes a helical shape within said capsule.

17. The guide wire control device of claim 14, wherein said capsule includes a prosthetic heart valve.

18. The guide wire control device of claim 14, wherein said releasable lock mechanism includes a threaded rotating member.

19. The guide wire control device of claim 14, wherein a cover is fixed to said sleeve.

20. The guide wire control device of claim 14, wherein said sleeve includes at least one flexible tab.

\* \* \* \* \*